United States Patent [19]

Kiyoura et al.

[11] Patent Number: 5,382,696
[45] Date of Patent: Jan. 17, 1995

[54] METHOD FOR PREPARING METHYLAMINES

[75] Inventors: Tadamitsu Kiyoura; Kazuhiro Terada, both of Kanagawa, Japan

[73] Assignee: Mitsui Toatsu Chemicals, Incorporated, Tokyo, Japan

[21] Appl. No.: 132,186

[22] Filed: Oct. 6, 1993

[30] Foreign Application Priority Data

Oct. 16, 1992 [JP] Japan .................................. 4-278743
Dec. 11, 1992 [JP] Japan .................................. 4-332005
Apr. 23, 1993 [JP] Japan .................................. 5-097592

[51] Int. Cl.$^6$ ........................................ C07C 209/16
[52] U.S. Cl. ................................. 564/479; 502/64
[58] Field of Search ....................... 564/479; 502/64

[56] References Cited

U.S. PATENT DOCUMENTS

| | | | |
|---|---|---|---|
| 4,683,334 | 7/1987 | Bergna et al. | 564/474 |
| 4,752,596 | 6/1988 | Bergna et al. | 502/64 |
| 4,918,233 | 4/1990 | Deeba et al. | 564/479 |
| 5,137,854 | 8/1992 | Segawa et al. | 502/64 |
| 5,210,308 | 5/1993 | Segawa et al. | 564/479 |

FOREIGN PATENT DOCUMENTS 324267 7/1989 European Pat. Off. .
4105188 8/1991 Germany .

*Primary Examiner*—Glennon H. Hollrah
*Assistant Examiner*—Scott C. Rand
*Attorney, Agent, or Firm*—Burns, Doane, Swecker & Mathis

[57] ABSTRACT

A method for selectively preparing dimethylamine and monomethylamine, while the production of trimethylamine is inhibited to a sufficiently low level. The method comprises carrying out a gaseous reaction of methanol and ammonia by the use of a mordenite modified with a silylating agent by a silylation treatment in a liquid phase. According to the present invention, recycling trimethylamine is unnecessary, and the amount of steam or the like to be used can be decreased.

10 Claims, No Drawings

METHOD FOR PREPARING METHYLAMINES

BACKGROUND OF THE INVENTION (i) Field of the Invention

The present invention relates to a method for preparing amines, and more specifically, it relates to a method for preparing methylamines from methanol and ammonia in which monomethylamine and dimethylamine are obtained in larger amounts, while the production of trimethylamine is inhibited to a sufficiently low level. The methylamines obtained by the method of the present invention are useful as raw materials for the manufacture of solvents and various intermediates of organic synthesis.

(ii) Description of the Prior Art

Methylamines, i.e., monomethylamine, dimethylamine and trimethylamine have been prepared by a method in which methanol or a mixture of methanol and dimethyl ether is reacted with ammonia, a method in which prussic acid is subjected to catalytic reduction, or the like.

These methylamines are produced as a mixture of monomethylamine, dimethylamine and trimethylamine, and they have independent applications, respectively. On the other hand, the demand of these methylamines is localized on dimethylamine and monomethylamine, and so trimethylamine is nowadays in little demand. The methylamines obtained by the reaction of methanol and ammonia in the presence of a conventional amorphous silica-alumina catalyst contain trimethylamine as a main component, and the process using this catalyst has the drawback that the production of dimethylamine which is in great demand is insufficient.

In order to overcome this drawback, U.S. Pat. No. 3,384,667 has suggested a technique in which a dehydrated crystalline aluminosilicate (a zeolite) having a pore diameter of 5–10 Å is used as a catalyst in the reaction of an alcohol having 1 to 18 carbon atoms with ammonia to predominantly produce monoamine and diamine over triamine. Furthermore, as zeolites suitable for the above-mentioned reaction, natural zeolites and synthetic zeolites are recited. That is, this U.S. patent discloses that examples of the desirable natural zeolites include faujasite, analcite, clinoptilolite, ferrierite, chabazite, gmelinite, levynite, erionite and mordenite. It is also disclosed that examples of the desirable synthetic zeolites include X type, Y type and A type zeolites.

There are known a method which comprises mixing methanol with ammonia in a specific ratio, and then carrying out the reaction in the presence of a catalyst such as mordenite to form monomethylamine in a surprisingly large amount (Japanese Patent Application Laid-open No. 113747/1981), and a method which comprises disproportionating monomethylamine on a crystalline aluminosilicate selected from Na mordenites to prepare dimethylamine with a high selectivity (Japanese Patent Application Laid-open No. 46846/1981).

In addition, there are also known a method in which a natural mineral is used as a mordenite in the same manner as in the above-mentioned U.S. Pat. No. 3,384,667 (Japanese Patent Application Laid-open No. 169444/1982), a method in which a mordenite ion-exchanged with lanthanum ions is used as the catalyst (Japanese Patent Application Laid-open No. 49340/1983), a method in which a mordenite containing an ion-exchanged alkaline metal in a specifically limited amount range is used as the catalyst (Japanese Patent Application Laid-open No. 210050/1984), a method in which a steam-treated mordenite is used as the catalyst (Japanese Patent Application Laid-open No. 227841/1984), a method in which an A type zeolite having a low binder content is used as the catalyst (Japanese Patent Application Laid-open No. 69846/1983), and a method in which a Rho type (ZK-5) zeolite is used as the catalyst.

When the zeolite catalyst is used by any of the above-mentioned methods, the production of trimethylamine can be inhibited, but for the purpose of inhibiting the production of trimethylamine to zero or substantially zero, some methods are also known in which a mordenite having pores treated by CVD (chemical vapor deposition) of silicon tetrachloride is used as the catalyst (Japanese Patent Application Laid-open No. 262540/1991; J. Catal., Vol. 131, pp. 482 (1991); and U.S. Pat. No. 5,137,854). Another method is also present in which chabazite, erionite, ZK-5 or a Rho type zeolite deposited or modified with compounds of silicon, aluminum, phosphorus or boron is used as the catalyst to restrict the production of trimethylamine (Japanese Patent Application Laid-open No. 254256/1986, and U.S. Pat. No. 4,683,334). Moreover, there is also known a method which comprises reacting an alcohol with ammonia by the use of SAPO of a non-zeolite molecular sieve as the catalyst to obtain alkylamines (Japanese Patent Application Laid-open No. 734/1990).

As described above, the production of trimethylamine which is in little demand can be inhibited to a low level by using any of the various already disclosed zeolite-based catalysts in the reaction of methanol and ammonia, so that the production of dimethylamine which is in great demand can be increased. However, even if the zeolite-based compound is used as the catalyst, the production ratio of trimethylamine can be merely restricted to usually 10%, or at most about 5%. If the production of trimethylamine can be inhibited to about 1 to 3%, it is not necessary to recycle trimethylamine which is in little demand to the reaction system for disproportionation, and as a result, a manufacturing process can be simplified and utilities, steam or the like, to be used can be decreased.

As a method for decreasing the production of trimethylamine to several percent, there is the above-mentioned method disclosed in Japanese Patent Application Laid-open No. 262540/1991 (U.S. Pat. No. 5,137,854) in which a mordenite deposited with silicon tetrachloride by a CVD treatment is used as the catalyst. However, this method can be easily carried out on a laboratory scale, but it is difficult to industrially manufacture a large amount of the catalyst for use in preparing methylamines.

In the above-mentioned method in which ZK-5 or a Rho type zeolite treated with silicon, aluminum, phosphorus or a boron compound is used to inhibit the production of trimethylamine to several percent (U.S. Pat. No. 4,683,334), there is the drawback that a specific synthetic zeolite such as ZK-5 or Rho is required to be used.

SUMMARY OF THE INVENTION

An object of the present invention is to provide a method not having such problems as described above, i.e., a method for industrially preparing methylamines by which the production of dimethylamine and monomethylamine is increased and the production of trimethylamine is decreased even to several percent or less, particularly about 1%.

The present inventors have conducted research on an industrial manufacturing process by which the production of trimethylamine is inhibited to an extremely low level and the production of monomethylamine and dimethylamine is increased. As a result, they have found that the production of trimethylamine can be decreased by the use of a specific catalyst in the reaction of methanol and ammonia. This specific catalyst is formed by treating a mordenite with a silylating agent in a liquid phase, and in a certain case, the production of trimethylamine can be inhibited to 1% or less by using the catalyst. A synthetic mordenite is industrially available and an inexpensive natural mordenite is also available in large quantities. In consequence, the present invention has been completed.

That is, the present invention is directed to a method for preparing methylamines which comprises reacting methanol with ammonia in a gaseous phase in the presence of a catalyst comprising a mordenite subjected to at least one silylation treatment with a silylating agent in a liquid phase, and then subjected to a heat treatment.

In the method for preparing methylamines by the reaction of methanol and ammonia in a gaseous phase, a modified mordenite subjected to a silylation treatment with a silylating agent in a liquid phase is used as a catalyst, whereby the production ratio of trimethylamine can be reduced to less than 5%, particularly a low level of about 1%. In consequence, a process where trimethylamine is disproportionated and then recycled through a reaction system can be omitted, and thus a methylamine manufacturing process can be simplified. In addition, the amount of steam to be used can be decreased. Accordingly, the present invention permits the industrially advantageous preparation of methylamines.

DETAILED DESCRIPTION OF THE INVENTION

A typical mordenite which has often been heretofore used in a reaction for preparing methylamines from methanol and ammonia is a crystalline aluminosilicate represented by $Na_8(Al_8Si_{40}O_{96}) \cdot 24H_2O$ (ATLAS OF ZEOLITE STRUCTURE TYPES, W. M. Meier and D. H. Olson, Butterworths, 1987). Alternatively, the mordenite can be represented by $Me_{1/n}(AlSi_5O_{12}) \cdot 3H_2O$ (Me is an alkali metal, an alkaline earth metal or a hydrogen atom, and n is 1 or 2) (Japanese Patent Application Laid-open Nos. 169444/1982 and 210050/1984).

In any case, in the typical mordenite, an Si/Al ratio is about 5 and a silica/alumina ($SiO_2/Al_2O_3$) ratio is about 10, irrespective of natural products or synthetic products (trade name ZEOLON ™, made by Norton Co., Ltd.; trade name LZM-8 ™, made by UCC; and trade name CM-180 ™, made by La Grande Paroisse Inc.). The mordenite in which the silica/alumina ratio is more than 11 is not known except some for specific synthetic products.

Accordingly, the mordenite which can be used in the method of the present invention has a silica/alumina ratio of about 10, or 10 or more. If a mordenite having a silica/alumina ratio of 10 or more is used, the catalytic activity is slightly low, but the deposition of carbon on the catalyst is decreased, so that the life of the catalyst can be prolonged. If a silica/alumina ratio of about 10 is desired, the typical synthetic or natural mordenite is used. The mordenite having a silica/alumina ratio of 11 or more can be prepared by treating the typical mordenite with an acid, or by subjecting the mordenite to an ordinary process such as a combination of the acid treatment and a stream treatment. Alternatively, the mordenite having a silica/alumina ratio of 11 or more can be formed by first preparing a gel-like slurry having a composition

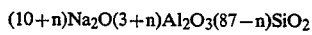

$$(10+n)Na_2O \cdot (3+n)Al_2O_3 \cdot (87-n)SiO_2$$

(wherein n is in the range of from 0 to 4) from an aqueous sodium silicate solution and an aqueous aluminum chloride solution, and then subjecting the slurry to a hydrothermal synthesis at 130°–250° C. for a period of from 10 hours to several days [Am. Mineral., Vol. 65, pp. 1012 (1972)].

As the mordenite which will be subjected to a silylation treatment, a hydrogen ion type mordenite is usually often used because of showing a high activity, but a mordenite in which a part of the hydrogen ion type is replaced with a small amount of an alkali metal ion type can also be used in a certain case. The synthetic or natural mordenite is obtained as an Na ion type, and therefore, after ion-exchange with ammonium ions, thermal decomposition is carried out to convert the Na ion type into the hydrogen ion type (H-type). Alternatively, the Na type mordenite may be treated with a 1 to 3N mineral acid to obtain the hydrogen ion type.

When the Na content in the mordenite is 0.2% by weight or less, the mordenite shows a high catalytic activity. However, when the Na content is 3% by weight or less, the mordenite becomes the catalyst showing the practical activity. The content of K is preferably 5% by weight or less. The mordenite having a Ca content of 5% by weight or less and an Mg content of 2% by weight or less is often used.

Prior to the treatment of the mordenite with the silylating agent, the water content in the mordenite is regulated to a predetermined range. In general, the silylation treatment of the mordenite is carried out by dispersing the mordenite in a solution obtained by dissolving the silylating agent in a suitable solvent. In this case, the water content in the mordenite is decided in compliance with the kind of solvent to be used.

When the solvent is compatible with water, such as a lower alcohol, it is preferable that the water content in the mordenite is substantially zero. However, if the water content is 4% by weight or less, a catalyst having a high selectivity can be prepared.

In order to make the water content in the mordenite substantially zero, the mordenite is calcined at a temperature of from 350° to 600° C.

When the solvent is not uniformly mixed with water to form a two-liquid phase, such as benzene, the water content in the mordenite is in the range of from 3 to 40% by weight, preferably from 5 to 30% by weight. If the water content deviates from the above-mentioned range, it is difficult to maintain the production of trimethylamine by the silylated catalyst at a low level of about 1%. The regulation of the water content in the mordenite can be carried out in various manners, and for example, the following manner is convenient.

The mordenite which has been ion-exchanged to the hydrogen ion type, washed with water, collected by filtration, and then dried is first calcined at 400°–600° C. to make the water content in the mordenite zero, and then the calcined mordenite is allowed to adsorb water vapor at about 0° to 60° C. under a water vapor pressure, whereby 3 to 40% by weight of water is imparted to the mordenite. In the case of a laboratory scale, a vessel containing water is put in the lower part of a desiccator, and the mordenite is placed in the upper part of the desiccator. Afterward, it is allowed to stand at room temperature for a period of 10 to 30 hours, so that 5 to 20% by weight of water is imparted to the mordenite. Alternatively, the mordenite which has been ion-exchanged to the hydrogen ion type, washed with water and then collected by filtration is dried at a temperature of from 100° to 150° C., whereby a water content in the above-mentioned range can be imparted to the mordenite. When the water content is regulated by this procedure, water and a trace amount of an acid are coexistent in the pores of the mordenite, and they conveniently function as catalysts during the silylation reaction in liquid phase. That is, water containing the trace amount of the acid occluded in the pores of the mordenite is gradually outwardly released, and it extremely effectively functions to smoothly advance a hydrolytic reaction after the silylation treatment and the silylation reaction.

Examples of the silylating agent for use in the silylation treatment include tetraalkoxysilanes such as tetramethoxysilane and tetraethoxysilane, dimer to hexamer of tetraalkoxysilanes, silicon tetrachloride, dimethyldichlorosilane, trimethylchlorosilane, tetramethyldisilazane and hexamethyldisilazane.

The silylation treatment of the mordenite is carried out in a liquid phase. The silylating agent may be directly used, but in general, it is dissolved in a suitable solvent and then used.

Examples of the solvent which is often used to form a two-liquid phase with water include aliphatic and alicyclic hydrocarbons such as hexane, octane and cyclohexane, aromatic hydrocarbons such as benzene, toluene and xylene, and ethers such as ethyl ether and isopropyl ether.

Examples of the solvent compatible with water which is often used include lower alcohols such as methanol, ethanol and isopropyl alcohol, and alkyl ethers of ethylene glycol such as ethylene glycol monomethyl ether and ethylene glycol monoethyl ether.

The desirable solvents are preferably selected in compliance with the kind of silylating agent to be used.

The amount of the silylating agent to be used is such that a silicon content in the silylating agent is in the range of from 1 to 15% by weight based on the weight of the mordenite to be used in terms of silicon oxide.

The concentration of the silylating agent in the solvent is in the range of from 2 to 30% by weight. When a large amount of water is present in the solvent to be used, the silylating agent is hydrolyzed in vain, and it is preferable that water which is an impurity is slightly contained in the solvent.

The above-mentioned silylating agent is dissolved in the above-mentioned solvent to form a silylating agent solution, and the mordenite is then suspended in the silylating agent solution to carry out the silylation treatment for the mordenite, whereby a silicon compound is deposited and fixed on the mordenite.

The temperature at which the silylation treatment is carried out is in the range of from room temperature to a boiling point of the solution, and the temperatures in the range of from 20° to 200° C. are often used. When the treatment is given under the application of pressure, the treatment temperature can be further raised.

The time which is taken for the silylation treatment depends mainly upon the treatment temperature, but a treatment time of from 6 to 100 hours is often used at a treatment temperature in the vicinity of room temperature and a time of from 2 to 20 hours is often used at the temperature of from 60° to 90° C.

After completion of the silylation treatment, the mordenite is separated from the treatment solution by a usual manner such as filtration or centrifugal separation, and then heated under the atmosphere of an inert gas such as nitrogen or under reduced pressure to remove the adhered or adsorbed organic solvent therefrom. Next, the mordenite is heated at 300°–600° C. in the atmosphere of air or oxygen to obtain a catalyst.

The above-mentioned silylation treatment of the mordenite with the silylating agent is not limited to one operation but it may be repeated plural times. In particular, when the dried mordenite is subjected to the silylation treatment by the use of the solvent compatible with water, the silylation treatment is repeated several times to obtain the catalyst which permits decreasing the production of trimethylamine to about 1%. In the case that the moisture-conditioned mordenite is subjected to the silylation treatment by the use of the solvent for forming a two-liquid phase with water, the catalyst capable of reducing the production of trimethylamine to a sufficient low level can usually be obtained by the one silylation treatment operation, and therefore the plural treatment operations are unnecessary in many cases.

In the method of the present invention for preparing methylamines from methanol and ammonia by using the silylated mordenite as a catalyst, in order to further decrease the production of trimethylamine, a catalyst is used which can be obtained by bringing the silylated mordenite into contact with a compound represented by $NR^1R^2R^3$, and then subjecting the same to a heat treatment. In the above-mentioned formula, each of $R^1$, $R^2$ and $R^3$ is independently a hydrogen atom; a non-substituted, an amino group-substituted or a hydroxyl group-substituted alkyl group; a non-substituted, an amino group-substituted or a hydroxyl group-substituted cycloalkyl group; or a non-substituted, an amino group-substituted or a hydroxyl group-substituted aryl group. Examples of the alkyl group include methyl, ethyl, propyl, butyl, pentyl, hexyl, heptyl, octyl, nonyl and decyl having 1 to 10 carbon atoms, and examples of the cycloalkyl group include cyclopentyl and cyclohexyl. Furthermore, examples of the aryl group include phenyl, tolyl, xylyl, naphthyl and biphenyl having 6 to 12 carbon atoms.

Typical examples of $NR^1R^2R^3$ include ammonia, monomethylamine, dimethylamine, trimethylamine, monoethylamine, diethylamine, triethylamine, monopropylamine, dipropylamine, tripropylamine, monobutylamine, dibutylamine, tributylamine, monopentylamine, dipentylamine, tripentylamine, monoethanolamine, diethanolamine, triethanolamine, monocyclohexylamine, dicyclohexylamine, aniline, toluidine and naphthylamine, and they are used for the above-mentioned contact treatment singly or in the form of a mixture of two or more thereof.

The silylated mordenite is impregnated directly with the above-mentioned nitrogen-containing compound or with an aqueous solution or an alcohol solution of the compound, or it is brought into contact with the compound by spraying the solution.

The amount of the nitrogen-containing compound to be used in the treatment is in the range of from 2 to 20% by weight based on the weight of the mordenite. A concentration of the solution containing the nitrogen-containing compound is in the range of from 1 to 30% by weight.

The temperature at which the mordenite is brought into contact with the nitrogen-containing compound is in the range of from room temperature to 400° C., and the contact time is not particularly limited but it is preferably in the range of from 1 hour to 1 day.

As another means for bringing the mordenite into contact with the nitrogen-containing compound, there may be used a method which comprises filling a reactor of an apparatus for a methylamine synthesis reaction with the silylated mordenite, reacting methanol with ammonia at 250°–350° C. under 0 to 30 kg/cm$^2$G, and then bringing the resultant methylamine into contact with the silylated mordenite in the system. In the reactor, the time required for the above-mentioned contact treatment operation is in the range of from several hours to 60 hours, and the contact time usually used is in the range of from 3 to 30 hours.

Next, for the silylated mordenite which has been brought into contact with the nitrogen-containing compound, a heat treatment is carried out.

The temperature of the heat treatment is suitably in the range of from 400° to 600° C., and the time required for the heat treatment is from several hours to 50 hours. The atmosphere in which the heat treatment is carried out is an inert gas such as nitrogen, an oxygen-containing gas such as air, a flue gas or water vapor, and no particular restriction is put on the kind of atmosphere. The pressure of the treatment atmosphere is often used in the range of from 0 to 30 kg/cm$^2$G, but it is convenient that the heat treatment is carried out in the vicinity of 0 kg/cm$^2$G.

In the process in which the heat treatment is carried out after the contact with the nitrogen-containing compound, the dried mordenite can be applied to the silylated mordenite catalyst in the solvent compatible with water, and this technique is effective to reduce the production of trimethylamine to a level of about 1%. In particular, this technique is effective in the case that the above-mentioned silylation treatment is done once.

If the mordenite which is the starting material of the catalyst is in the form of molded grains or tablets, it can be directly used as the catalyst without any additional treatment. If it is in the state of powder, it is extruded or tableted, and then used as the catalyst.

The reaction raw materials which can be used in the method of the present invention are ammonia and methanol or a mixture of methanol and dimethyl ether. A molar ratio of ammonia to methanol is 1:0.5 or more, preferably 1:1 to 1:10, and the range of from 1:1 to 1:4 is often used.

The feed of the reaction gas which is fed to a catalyst layer is in the range of from 200 to 20,000/hr in terms of a gaseous hourly space velocity (GHSV), and the pressure for the reaction which is often used is in the range of from 0 to 30 kg/cm$^2$G, preferably from 10 to 25 kg/cm$^2$G.

The temperature of the catalyst layer in the practice of the reaction is often in the range of from 250° to 450° C., preferably from 250° to 350° C.

A reactor which can be used to carry out the method of the present invention is a usual fixed-bed or fluidized bed reactor. The reaction between methanol and ammonia in the present invention is an exothermic reaction of about 14 KCal/mol, and therefore in the case that the fixed-bed reactor is used, it is important to remove heat of reaction for the purpose of maintaining the production of trimethylamine at a low level. That is, it is necessary to maintain a hot spot of the catalyst bed at the upper limit or less of the above-mentioned reaction temperature. For this purpose, the employment of a shell-and-tube reactor is preferable. A tube diameter of the shell-and-tube reactor is often in the range of from 1 to 3 inches.

From a gas at an outlet of the reactor, methylamines are separated and collected by a usual separating/purifying device, but according to the present invention, the production of trimethylamine is about several percent, and hence the equipment for trimethylamine separation is of small-scale and recycling trimethylamine through the reaction system is unnecessary, whereby the whole manufacturing process can be simplified. In addition, since the amount of materials to be recycled through the reaction system is decreased, the amount of utilities, steam or the like, can be reduced.

Now, the present invention will be described in reference to examples and reference examples. It should be noted that the scope of the present invention is not limited to these examples.

EXAMPLE 1

150 g of a synthetic mordenite were suspended in 1 liter of a 0.5N aqueous ammonium nitrate solution, and the resultant suspension was heated on an oil bath and then refluxed for 4 hours. The mordenite was collected by filtration and then suspended in a fresh 0.5N aqueous ammonium nitrate solution, and a similar operation was then repeated three times in all. Afterward, filtration and water washing were carried out to obtain an ammonium type mordenite, and this mordenite was dried, and then calcined at 600° C. to change into an H-mordenite. An Na content in the mordenite was 0.13% by weight. This mordenite was preserved in a dry sealed container.

60 g of the above-mentioned H-mordenite were suspended in a solution obtained by dissolving 7.5 g of tetraethoxysilane in 100 g of ethanol, and the suspension was then heated and shaken at 60° C. for 8 hours. The mordenite was collected by filtration, washed with ethanol, heated at 350° C. for 3 hours in a nitrogen gas flow, and then heated at 500° C. for 5 hours in an air flow. The thus treated mordenite was molded into tablets having a size of 3 mm×3 mm, and they were used as a catalyst.

A stainless steel reaction tube having an inner diameter of 1 inch was filled with 40 g (64 ml) of the above-mentioned catalyst, and it was then heated from the outside with a sand fluid bath.

Methanol and ammonia were fed to the reaction tube through an evaporator under pressure at flow rates of 18 g/hr and 18.7 g/hr, respectively, and reaction was then carried out at a catalyst bed temperature of 310° C. under a pressure of 19 kg/cm$^2$G. Twenty hours after the beginning of the reaction, a gas at the outlet of the reaction tube was sampled and analyzed. As a result, the conversion of methanol was 90%, the selectivity of monomethylamine was 33.3%, the selectivity of dimethylamine was 63%, and the selectivity of trimethylamine was 3.7%.

EXAMPLE 2

110 g of a natural zeolite (mordenite content = about 70%) having a particle diameter of from 2 to 4 mm were thrown into 1 liter of 2N hydrochloric acid, followed by shaking at 50° C. for 10 hours. The zeolite was collected by filtration and then thrown into 1 liter of a fresh 1N hydrochloric acid, followed by shaking at 50° C. for 10 hours. The zeolite was collected by filtration, washed with water, dried, and then heated to 500° C. to obtain an H-mordenite. The thus obtained zeolite was substantially completely an H type, and an Na content was 0.15%.

50 g of the above-mentioned zeolite were thrown into 100 g of a methanol solution in which 7 g of tetramethoxysilane were dissolved, and the mixture was then shaken at room temperature (20°-25° C.) for 60 hours. The zeolite was collected by filtration, washed with methanol, heated at 350° C. for 2 hours in a nitrogen gas flow, and then further heated at 500° C. for 4 hours in an air flow. The thus treated particulate zeolite was directly used as a catalyst in reaction.

A stainless steel reaction tube having an inner diameter of 1 inch was filled with 40 g (60 ml) of the above-mentioned catalyst, and it was then heated from the outside with a sand fluid bath.

Methanol and ammonia were fed to the reaction tube through an evaporator under pressure at flow rates of 15 g/hr and 16 g/hr, respectively, and the reaction was then carried out at 310° C. under a pressure of 19 kg/cm$^2$G. Thirty hours after the beginning of the reaction, a gas at the outlet of the reaction tube was analyzed. As a result, the conversion of methanol was 90%, the selectivity of monomethylamine was 34.4%, the selectivity of dimethylamine was 62.1%, and the selectivity of trimethylamine was 3.5%.

Reference Example 1

50 g of a particulate zeolite of Example 2 were thrown into a solution obtained by dissolving 7 g of tetramethoxysilane in 100 g of benzene, and the mixture was then shaken at room temperature (20° to 25° C.) for 60 hours. The zeolite was collected by filtration, washed with benzene, heated at 350° C. for 3 hours in a nitrogen gas flow, and then further heated at 500° C. for 4 hours in an air flow. The thus obtained particulate zeolite was directly used as a catalyst in reaction.

A stainless steel reaction tube having an inner diameter of 1 inch was filled with 40 g (61 ml) of the above-mentioned catalyst, and it was then heated from the outside with a sand fluid bath.

Methanol and ammonia were fed to the reaction tube through an evaporator under pressure at flow rates of 15 g/hr and 16 g/hr, respectively, and the reaction was then carried out at 310° C. under a pressure of 19 kg/cm$^2$G. Thirty hours after the beginning of the reaction, a gas at the outlet of the reaction tube was analyzed. As a result, the conversion of methanol was 90%, the selectivity of monomethylamine was 28.4%, the selectivity of dimethylamine was 62.5%, and the selectivity of trimethylamine was 9.1%. In this example, the substantially anhydrous mordenite and the silylating solvent for forming a two-liquid phase with water were used. That is, the combination of the anhydrous mordenite and the solvent for forming the two-liquid phase with water could not inhibit the production of trimethylamine to a sufficiently low level.

EXAMPLE 3

200 g of a particulate mordenite (average particle diameter = 2-3 mm) were gently stirred for 4 hours in 2 liters of a 0.2N aqueous KCl solution, washed with water, and then collected by filtration. Next, the collected mordenite was thrown into 2 liters of a 1.2N aqueous HCl solution, gently stirred for 4 hours, and then collected by filtration. Afterward, 2 liters of a fresh 1.2N aqueous HCl solution were added to the mordenite, and then allowed to stand overnight. The mordenite was washed with water, collected by filtration, dried, and then calcined at 500° C. to obtain an H-mordenite. In the obtained H-mordenite, an Na content was 0.11% by weight, and a K content was 2.3% by weight.

50 g of the above-mentioned mordenite were sampled and then thrown into a solution obtained by dissolving 9 g of tetraethoxysilane in 70 g of methanol, followed by shaking at room temperature for 6 hours. The solid was collected by filtration, and calcined at 250° C. for 1 hour in a nitrogen gas flow and then at 500° C. for 2 hours in an air atmosphere to achieve a silylation treatment. Furthermore, the above-mentioned silylation treatment was repeated 4 times to prepare a catalyst.

40 g of the obtained catalyst were sampled, and a methylamine synthetic reaction was tested under the same reaction conditions by the same apparatus as in Example 1. 100 hours after the beginning of the reaction, the resultant product was quantitatively analyzed. As a result, the conversion of methanol was 91%, the selectivity of monomethylamine was 35.6%, the selectivity of dimethylamine was 63.4%, and the selectivity of trimethylamine was 1.0%.

EXAMPLE 4

150 g of a mordenite were suspended in 1 liter of a 0.5N aqueous ammonium nitrate solution, and the resultant suspension was heated on an oil bath and then refluxed for 8 hours. The mordenite was collected by filtration and then thrown into a fresh 0.5N aqueous ammonium nitrate solution, and a similar operation was then repeated three times in all. Afterward, filtration and water washing were carried out to obtain an ammonium type mordenite, and this mordenite was dried, and then calcined at 550° C. to change into an H-mordenite. This mordenite was preserved in a dry sealed container.

A container filled with water was put in the lower part of a desiccator, and 60 g of the above-mentioned mordenite were put in the upper part of the desiccator. Afterward, the mordenite was allowed to stand at room temperature for 20 hours, thereby imparting about 13% by weight of water to the mordenite.

60 g of the above-mentioned H-mordenite were suspended in a solution obtained by dissolving 12 g of tetraethoxysilane in 100 g of benzene, and the suspension was then gently shaken at room temperature for 40 hours. The mordenite was collected by filtration, heated at 250° C. for 2 hours in a nitrogen gas flow, and then further heated at 500° C. for 4 hours in an air flow. The treated mordenite was molded into tablets having a size of 3 mm×3 mm, and it was used as a catalyst.

A stainless steel reaction tube having an inner diameter of 1 inch was filled with 40 g (64 ml) of the above-mentioned catalyst, and it was then heated from the outside with a sand fluid bath.

Methanol and ammonia were fed to the reaction tube through an evaporator under pressure at flow rates of 18 g/hr and 17 g/hr, respectively, and reaction was then carried out at a catalyst bed temperature of 310° C. under a pressure of 20 kg/cm²G. 100 hours after the beginning of the reaction, a gas at the outlet of the reaction tube was sampled and analyzed. As a result, the conversion of methanol was 90%, the selectivity of monomethylamine was 36.1%, the selectivity of dimethylamine was 63%, and the selectivity of trimethylamine was 0.9%.

Reference Example 2

60 g of an H-mordenite prepared in Example 4 were calcined, and then, without moisture conditioning, suspended in a solution obtained by dissolving 12 g of tetraethoxysilane in 100 g of benzene, followed by shaking at room temperature for 40 hours. Afterward, the mordenite was collected by filtration, heated at 250° C. for 2 hours in a nitrogen gas flow, further heated at 450° C. for 4 hours in an air flow, and then molded into tablets having a size of 3 mm×3 mm. The thus prepared tablets were used as a catalyst.

A stainless steel reaction tube having an inner diameter of 1 inch was filled with 40 g (70 ml) of the above-mentioned catalyst, and the reaction for synthesizing methylamine from methanol and ammonia was tested under the same reaction conditions as in Example 4.

120 hours after the beginning of the reaction, a gas at the outlet of the reaction tube was sampled and analyzed. As a result, the conversion of methanol was 91%, the selectivity of monomethylamine was 28.5%, the selectivity of dimethylamine was 65.3%, and the selectivity of trimethylamine was 6.2%.

The combination of the mordenite which had not undergone the moisture conditioning and the silylating solvent for forming the two-liquid phase with water could not inhibit the production of trimethylamine to a sufficiently low level.

EXAMPLE 5

110 g of a natural zeolite (mordenite content = about 70%) having a particle diameter of from 2 to 3 mm were thrown into 1 liter of 2N hydrochloric acid, followed by shaking at 50° C. for 10 hours. The zeolite was collected by filtration and then thrown into 1 liter of a fresh 1N hydrochloric acid, followed by shaking at 50° C. for 10 hours. The zeolite was collected by filtration, and 1 liter of a fresh 1N hydrochloric acid was used and a similar operation was repeated. The zeolite was collected by filtration, washed with water, dried, and then heated to 500° C. to obtain an H-mordenite. The thus obtained zeolite is substantially completely an H type, and an Na content was 0.19%.

10% by weight of water were imparted to the calcined zeolite in the same manner as in Example 4. 50 g of the above-mentioned zeolite were thrown into 100 g of a toluene solution in which 4 g of tetramethoxysilane were dissolved, and the mixture was then shaken at room temperature (20°–25° C.) for 20 hours.

The zeolite was collected by filtration, heated at 300° C. for 2 hours in a nitrogen gas flow, and then further heated at 500° C. for 4 hours in an air flow. The thus treated particulate zeolite was directly used as a catalyst in the methylamine synthesis reaction.

A stainless steel reaction tube having an inner diameter of 1 inch was filled with 40 g (70 ml) of the above-mentioned catalyst, and it was then heated from the outside with a sand fluid bath.

Methanol and ammonia were fed to the reaction tube through an evaporator under pressure at flow rates of 16 g/hr and 16 g/hr, respectively, and the reaction was then carried out at 310° C. under a pressure of 19 kg/cm²G.

130 hours after the beginning of the reaction, a gas at the outlet of the reaction tube was analyzed. As a result, the conversion of methanol was 90%, the selectivity of monomethylamine was 34.8%, the selectivity of dimethylamine was 64.0%, and the selectivity of trimethylamine was 1.0%.

Reference Example 3

50 g (dry basis) of a particulate zeolite containing an H-mordenite of Example 5 and having a water content of 56% were thrown into a solution obtained by dissolving 10 g of tetramethoxysilane in 100 g of benzene, and the mixture was then shaken at room temperature (20° to 25° C.) for 20 hours. Next, the zeolite was collected by filtration, heated at 300° C. for 2 hours in a nitrogen gas flow, and then heated at 500° C. for 4 hours in an air flow. The thus obtained particulate zeolite was directly used as a catalyst in reaction.

A stainless steel reaction tube having an inner diameter of 1 inch was filled with 40 g (71 ml) of the above-mentioned catalyst, and it was then heated from the outside with a sand fluid bath.

Methanol and ammonia were fed to the reaction tube through an evaporator under pressure at flow rates of 16 g/hr and 16 g/hr, respectively, and the reaction was then carried out at 310° C. under a pressure of 19 kg/cm²G.

30 hours after the beginning of the reaction, a gas at the outlet of the reaction tube was analyzed. As a result, the conversion of methanol was 92%, the selectivity of monomethylamine was 29.4%, the selectivity of dimethylamine was 63.5%, and the selectivity of trimethylamine was 7.1%.

When the mordenite containing water in a larger amount than predetermined in the present invention was used, the production of trimethylamine could not be inhibited to a sufficient low level, even if the silylation treatment was carried out.

EXAMPLE 6

100 g of the same particulate zeolite as in Example 5 were thrown into 1 liter of 1N hydrochloric acid, and the mixture was then gently stirred at room temperature for 6 hours, followed by filtration. Next, a fresh 1N hydrochloric acid was added thereto, and a similar treatment was then carried out. Afterward, the zeolite was washed with water, and then collected by filtration to prepare a zeolite containing an H-mordenite. This zeolite was thrown into 1 liter of a 0.16N aqueous KCl solution, and the mixture was then allowed to stand at room temperature for 30 minutes, washed with water, collected by filtration, and then dried at 110° C. for 3 hours to regulate a water content to 10% by weight. In the thus obtained zeolite, an Na content was 0.12% by weight, and a K content was 3.2% by weight.

50 g of the above-mentioned zeolite were thrown into a solution obtained by dissolving 12 g of tetraethoxysilane in 80 g of toluene, and the mixture was then allowed to stand at room temperature for 16 hours. Next, the zeolite was collected by filtration, calcined at 250° C. for 2 hours in a nitrogen gas flow, and then further calcined at 500° C. for 2 hours in an air flow to prepare a catalyst.

The same reactor as in Example 4 was filled with 40 g of this catalyst, and the performance of the catalyst was tested under the same reaction conditions as in Example 5.

100 hours after the beginning of the reaction, the resultant product was analyzed. As a result, the conversion of methanol was 84%, the selectivity of monomethylamine was 39.1%, the selectivity of dimethylamine was 60.0%, and the selectivity of trimethylamine was 0.9%.

EXAMPLE 7

50 g of a zeolite containing an H-mordenite of Example 6 were thrown into a 0.2N aqueous NaCl solution, and the mixture was then allowed to stand for 30 minutes. Next, the zeolite was washed with water, collected by filtration, and then dried at 110° C. In the thus obtained zeolite, an Na content was 1.2% by weight, and a K content was 1.1% by weight.

The above-mentioned zeolite were thrown into a solution obtained by dissolving 12 g of tetraethoxysilane in 80 g of benzene, and the mixture was then allowed to stand at room temperature for 16 hours. Afterward, the zeolite was collected by filtration, calcined at 250° C. for 2 hours in a nitrogen gas flow, and then further calcined for 3 hours in an air flow to prepare a catalyst.

40 g of this catalyst were sampled, and the performance of the catalyst was tested under the same reaction conditions as in Example 6. As a result, the conversion of methanol was 85%, the selectivity of monomethylamine was 38.0%, the selectivity of dimethylamine was 61.1%, and the selectivity of trimethylamine was 0.9%.

EXAMPLE 8

150 g of a synthetic mordenite were suspended in 1 liter of a 0.5N aqueous ammonium nitrate solution, and the resultant suspension was heated on an oil bath and then refluxed for 4 hours. Next, the mordenite was collected by filtration and then suspended in a fresh 0.5N aqueous ammonium nitrate solution, and a similar operation was then repeated three times in all. Afterward, filtration and water washing were carried out to obtain an ammonium type mordenite, and this mordenite was dried, and then calcined at 600° C. to change into an H-mordenite. This mordenite was preserved in a dry sealed container.

60 g of the above-mentioned H-mordenite were suspended in a solution obtained by dissolving 7.5 g of tetraethoxysilane in 100 g of ethanol, and the suspension was then heated and shaken at 68° C. for 8 hours. Next, the mordenite was collected by filtration, washed with ethanol, heated at 350° C. for 3 hours in a nitrogen gas flow, and then further heated at 500° C. for 5 hours in an air flow. The thus treated mordenite was molded into tablets having a size of 3 mm×3 mm.

The thus obtained tablets were thrown into an aqueous solution in which monomethylamine, dimethylamine and trimethylamine were dissolved (the total concentration of the methylamines was 5%), and the tablets were then impregnated directly with the aqueous solution at room temperature for 2 hours. Next, the tablets were separated from the aqueous solution, and then thermally treated at 450° C. for 4 hours in an air atmosphere to prepare a catalyst.

A stainless steel reaction tube having an inner diameter of 1 inch was filled with 40 g (64 ml) of the above-mentioned catalyst, and it was then heated from the outside with a sand fluid bath.

Methanol and ammonia were fed to the reaction tube through an evaporator under pressure at flow rates of 18 g/hr and 18.7 g/hr, respectively, and reaction was then carried out at a catalyst bed temperature of 300° C. under a pressure of 19 kg/cm$^2$G. 20 hours after the beginning of the reaction, a gas at the outlet of the reaction tube was sampled and analyzed. As a result, the conversion of methanol was 90%, the selectivity of monomethylamine was 35.2%, the selectivity of dimethylamine was 63%, and the selectivity of trimethylamine was 1.8%.

EXAMPLE 9

A mordenite catalyst silylated in Example 8 was used in a methylamine synthesis, without being subjected to a nitrogen-compound treatment and a heat treatment.

A stainless steel reaction tube having an inner diameter of 1 inch was filled with 40 g (65 ml) of the above-mentioned catalyst, and the reaction for synthesizing methylamine from methanol and ammonia was tested under the same reaction conditions as in Example 8.

Twenty hours after the beginning of the reaction, a gas at the outlet of the reaction tube was sampled and analyzed. As a result, the conversion of methanol was 91%, the selectivity of monomethylamine was 31.1%, the selectivity of dimethylamine was 65.1%, and the selectivity of trimethylamine was 3.8%.

EXAMPLE 10

110 g of a natural zeolite having a particle diameter of 2 to 4 mm (a mordenite content = about 70%) were thrown into 1 liter of a 2N hydrochloric acid, and the mixture was then shaken at 50° C. for 10 hours. Next, the zeolite was collected by filtration, thrown into a fresh 1N hydrochloric acid, and then shaken at 60° C. for 10 hours. The thus treated zeolite was collected by filtration, washed with water, dried, and then heated up to 500° C. to obtain a zeolite containing an H-mordenite. The thus obtained zeolite was substantially completely an H type and had an Na content of 0.18%.

50 g of the above-mentioned zeolite were thrown into 100 g of a methanol solution in which 7 g of tetramethoxysilane were dissolved, and the mixture was then shaken at room temperature (20°-25° C.) for 20 hours. Afterward, the zeolite was collected by filtration, washed with methanol, heated at 350° C. for 2 hours in a nitrogen gas flow, and then further heat at 500° C. for 4 hours in an air flow. The thus obtained particulate zeolite was directly used as a catalyst in reaction.

A stainless steel reaction tube having an inner diameter of 1 inch was filled with 40 g (60 ml) of the above-mentioned catalyst, and it was then heated from the outside with a sand fluid bath.

Methanol and ammonia were fed to the reaction tube through an evaporator under pressure at flow rates of 19 g/hr and 20 g/hr, respectively, and reaction was then carried out at 305° C. under a pressure of 19 kg/cm$^2$G.

40 hours after the beginning of the reaction, a gas at the outlet of the reaction tube was analyzed. As a result, the conversion of methanol was 91%, the selectivity of monomethylamine was 34.3%, the selectivity of dimethylamine was 62.0%, and the selectivity of trimethylamine was 3.7%.

EXAMPLE 11

A reaction operation of methanol and ammonia was interrupted in the above-mentioned Example 10, and a nitrogen gas was caused to stream at 450° C. under 2 kg/cm²G at 100 ml/min on a catalyst bed to carry out the heat treatment of the catalyst of a silylated mordenite which had been brought into contact with a nitrogen-containing compound during a methylamine synthetic reaction in a reactor.

A heat treatment was carried out for 6 hours, and a synthetic reaction of methylamine was tested at a catalyst bed temperature of 307° C. by feeding methanol and ammonia under the same conditions as in Example 10.

30 hours after the beginning of the reaction, a gas at the outlet of the reaction tube was analyzed. As a result, the conversion of methanol was 89%, the selectivity of monomethylamine was 34.8%, the selectivity of dimethylamine was 63.5%, and the selectivity of trimethylamine was 1.7%.

EXAMPLE 12

50 g of a particulate mordenite converted into a hydrogen ion type (Na content=0.15% by weight, particle diameter=2-3 mm) were calcined at 500° C., cooled, thrown into 150 ml of a 0.05N aqueous HCl solution, and then allowed to stand for 1 hour. Next, the thus treated mordenite was collected by filtration, washed with 200 ml of deionized water, filtered with suction, and then dried at 130° C. for 3 hours. In this state, a water content in the mordenite was 10% by weight, and 0.01 mmol/g of HCl remained.

Afterward, the above-mentioned mordenite was thrown into a solution obtained by dissolving 5 g of tetraethoxysilane in 100 g of toluene, and a silylation treatment was then carried out at room temperature for 30 hours with gently shaking. Next, the mordenite was filtered with suction, calcined at 200° C. for 2 hours in an N₂ gas flow, and then further calcined at 500° C. for 3 hours in an air flow to prepare a catalyst.

A stainless steel reaction tube having an inner diameter of 1 inch was filled with 40 g (74 ml) of the catalyst, and methanol and ammonia were fed to the reaction tube through an evaporator at flow rates of 19 g/hr and 19 g/hr, respectively, and the reaction was then carried out at 294° C. under a pressure of 20 kg/cm²G.

sixty hours after the beginning of the reaction, a gas at the outlet of the reaction tube was analyzed, and as a result, the conversion of methanol was 94%, the selectivity of monomethylamine was 33.4%, the selectivity of dimethylamine was 64.0%, and the selectivity of trimethylamine was 2.6%.

What is claimed is:

1. A method for preparing methylamines which comprises reacting methanol with ammonia in a gaseous phase in the presence of a catalyst wherein the catalyst is (a) a mordenite obtained by subjecting a dry mordenite of the hydrogen ion type to at least one silylation treatment with a silylating agent in a solvent compatible with water, and then subjecting the silylated mordenite to heat treatment, or (b) a mordenite obtained by subjecting a mordenite of the hydrogen ion type occluding 3 to 40% by weight of water and an acid to at least one silylation treatment with a silylating agent in a solvent for forming a two-liquid layer with water, and then subjecting the silylated mordenite to heat treatment.

2. The method for preparing methylamines according to claim 1 wherein said silylating agent is a tetraalkoxysilane.

3. The method for preparing methylamines according to claim 1 wherein the dry mordenite has a water content of 4% by weight or less.

4. The method for preparing methylamines according to claim 3 wherein said solvent compatible with water is an alcohol.

5. The method for preparing methylamines according to claim 1 wherein said catalyst is a catalyst prepared by bringing said silylated mordenite into contact with a compound represented by the formula $NR^1R^2R^3$ wherein each of $R^1$, $R^2$ and $R^3$ is independently a hydrogen atom; a non-substituted, an amino group-substituted or a hydroxyl group-substituted alkyl group; a non-substituted, an amino group-substituted or a hydroxyl group-substituted cycloalkyl group; or a non-substituted, an amino group-substituted or a hydroxyl group-substituted aryl group, and then subjecting said mordenite to a heat treatment at 400° to 600° C.

6. The method for preparing methylamines according to claim 1 wherein said mordenite to be subjected to said silylation treatment or said silylated mordenite has a sodium content of 3% by weight or less.

7. The method for preparing methylamines according to claim 6 wherein said mordenite to be subjected to said silylation treatment or said silylated mordenite has a sodium content of 0.2% by weight or less.

8. The method for preparing methylamines according to claim 1 wherein said mordenite to be subjected to said silylation treatment or said silylated mordenite has a potassium content of 5% by weight or less.

9. The method for preparing methylamines according to claim 1 wherein in reacting methanol with ammonia, temperature is in the range of from 250° to 350° C., pressure is in the range of from 0 to 30 kg/cm²G, and a molar ratio of ammonia to methanol is in the range of from 1:1 to 1:4.

10. The method for preparing methylamines according to claim 1 wherein the reaction of methanol and ammonia is carried out in a shell-and-tube reactor.

* * * * *